(12) United States Patent
Lue et al.

(10) Patent No.: US 7,910,873 B2
(45) Date of Patent: Mar. 22, 2011

(54) BIOCHIP MICROSYSTEM FOR BIOINFORMATICS RECOGNITION AND ANALYSIS

(75) Inventors: Jaw-Chyng Lue, Los Angeles, CA (US); Wai-Chi Fang, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 685 days.

(21) Appl. No.: 11/982,838

(22) Filed: Nov. 5, 2007

(65) Prior Publication Data

US 2009/0048125 A1 Feb. 19, 2009

Related U.S. Application Data

(60) Provisional application No. 60/856,512, filed on Nov. 3, 2006.

(51) Int. Cl.
*G01J 1/42* (2006.01)

(52) U.S. Cl. ............ 250/208.2; 250/214.1; 250/214 R; 348/294; 348/302; 257/431

(58) Field of Classification Search ............... 250/208.1, 250/214, 214 R, 208.2; 348/281, 294, 302; 257/431

See application file for complete search history.

(56) References Cited

U.S. PATENT DOCUMENTS

| | | | | |
|---|---|---|---|---|
| 4,243,882 A | * | 1/1981 | Yasujima et al. | ........ 250/339.06 |
| 6,750,437 B2 | * | 6/2004 | Yamashita et al. | ......... 250/208.1 |
| 2002/0139936 A1 | * | 10/2002 | Dumas | ....................... 250/458.1 |
| 2006/0046332 A1 | * | 3/2006 | Derderian et al. | ............. 438/28 |

* cited by examiner

*Primary Examiner* — Georgia Y Epps
*Assistant Examiner* — Francis M Legasse, Jr.
(74) *Attorney, Agent, or Firm* — Berliner & Associates

(57) ABSTRACT

A system with applications in pattern recognition, or classification, of DNA assay samples. Because DNA reference and sample material in wells of an assay may be caused to fluoresce depending upon dye added to the material, the resulting light may be imaged onto an embodiment comprising an array of photodetectors and an adaptive neural network, with applications to DNA analysis. Other embodiments are described and claimed.

19 Claims, 5 Drawing Sheets

> US 7,910,873 B2

BIOCHIP MICROSYSTEM FOR BIOINFORMATICS RECOGNITION AND ANALYSIS

PRIORITY CLAIM

This application claims the benefit of U.S. Provisional Application No. 60/856,512, filed 3 Nov. 2007.

GOVERNMENT INTEREST

The invention described herein was made in the performance of work under a NASA contract, and is subject to the provisions of Public Law 96-517 (35 USC 202) in which the Contractor has elected to retain title.

FIELD

Embodiments relate to recognition of DNA material using an optical and electronic system.

BACKGROUND

Genetic material may be analyzed by placing DNA (Deoxyribonucleic acid) material in an array of wells (dots). Polymerase chain reaction (PCR) amplification is often used in genetic analysis, where the PCR amplification augments the amount of DNA material placed in a well. Fluorescent dyes, such as CY3 or CY5, may be added to the DNA material, so that it fluoresces when excited by monochromatic light. Because with PCR amplification there may be different growth rates of DNA material from well to well, sample and reference channels may be set up whereby in each well, there is reference DNA and sample DNA. Fluorescent dye of one type may be used for the sample DNA, and fluorescent dye of another type may be used for the reference DNA.

This method also reduces the sources of variability and noise due to various aspects of an individual spot that affect both specimens (DNA sample and reference) similarly. In order to accurately calculate the density of the sample DNA material in a particular well after PCR amplification, the integral of the total fluorescence intensity (presumably representing the density of the DNA material inside the well) from the topological profile of the well is usually computed. The logarithmic value of the ratio of the two intensities of the fluorescent dye labeled specimens (one value for the sample specimen, the other value for the reference specimen) measured from the same well is calculated based on the assay's fluorescence image. The ratio of the two intensities would provide the normalized population of the gene material in the well, disregarding the initial population density.

In most of the available commercial solutions, the assay's fluorescence image is usually scanned by a color scanner with high resolution and then transferred to a computer for image analysis. The profile analysis software usually computes the normalized intensity of each well sequentially. The intensity of the fluorescence is usually relatively low. Using higher excitation light intensity or increasing detection time may lead to brighter fluorescence patterns. However, lower power consumption and faster detection may be preferable. Furthermore, some fixed-pattern noises in the input pattern may exist (e.g., fixed pattern noises created by scattered lights, or non-uniformity of the detector array response). These noises may introduce errors in the measurement of the density of the DNA materials The development of low-cost portable instruments for rapidly analyzing genetic assays in noisy environments and with relatively low intensity of fluorescence would be of utility in medical services.

DESCRIPTION OF EMBODIMENTS

In the description that follows, the scope of the term "some embodiments" is not to be so limited as to mean more than one embodiment, but rather, the scope may include one embodiment, more than one embodiment, or perhaps all embodiments.

Figure 1:
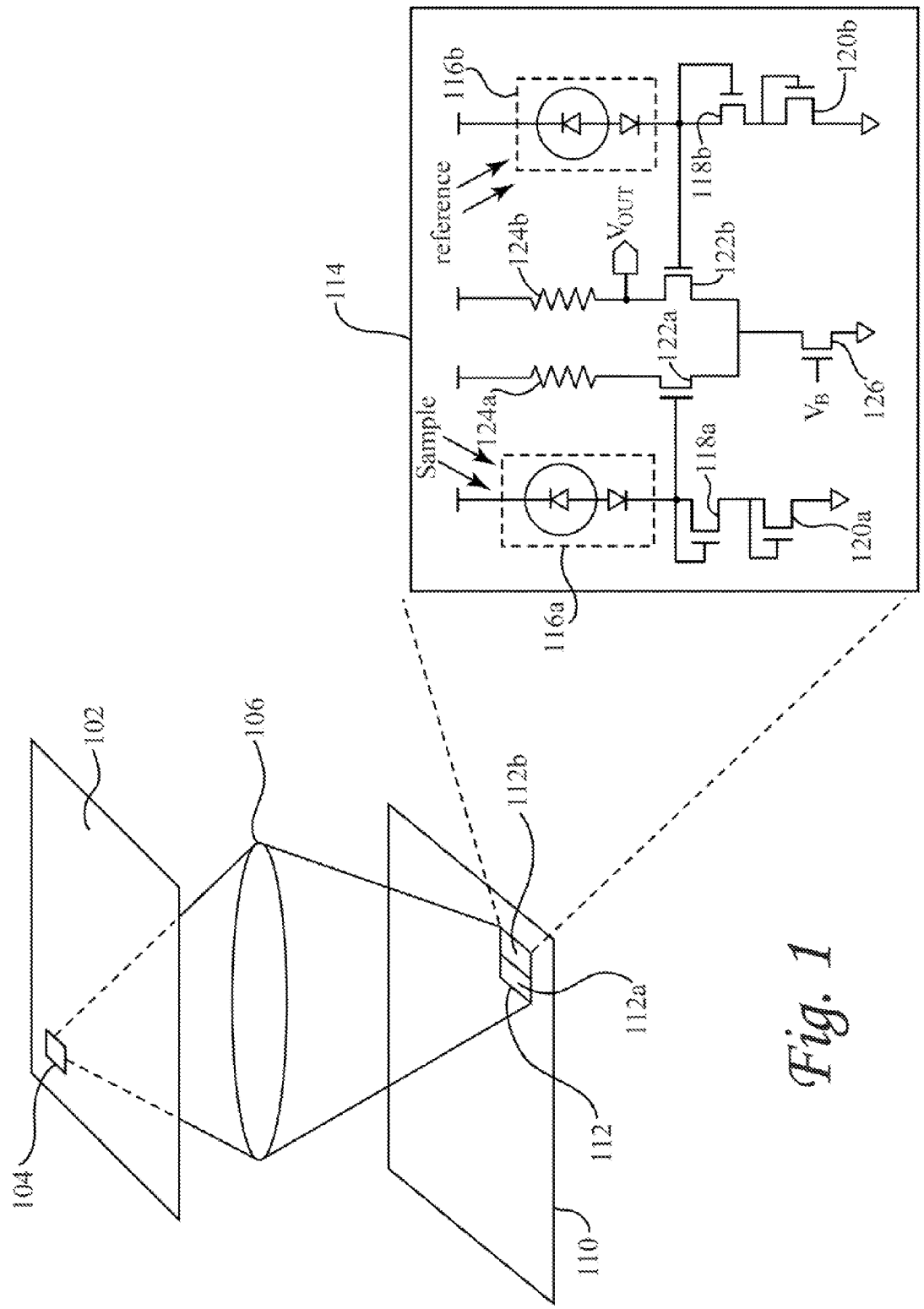
FIG. 1 illustrates a system for recognizing a pattern among a DNA sample assay according to an embodiment.

FIG. 1 illustrates various components of an embodiment in an exploded view. Assay array 102 comprises an array of dual-labeled gene wells (dots). For simplicity of illustration, only one well, labeled 104, is illustrated. Each well comprises reference DNA material and sample DNA material. The method of PCR amplification is applied to the array of wells in which a first dye is added to the sample DNA material and a second dye is added to the reference DNA material. When excited by light, the reference and sample DNA material may be made to fluoresce. The intensity of the fluorescence is indicative of the amount of DNA sample or reference material. The excitation light for the sample DNA material will for many instances have a different spectrum than the excitation light for the reference DNA material. The light given off by the sample DNA material will usually have a different spectrum than the light given off by the reference DNA material, depending upon the dyes, and usually the light given off by the reference and sample DNA material will have a spectrum different from their respective excitations. For some embodiments, the excitation may be monochromatic light. The monochromatic light may be realized by using optical notch filters in front of a relatively broad light source.

For example, for some embodiments CY3 and CY5 dyes may be used, where the DNA material to which CY3 has been added is excited by monochromatic light having a center frequency (wavelength) of 535 nm and a bandwidth of 10 nm, and the DNA material to which CY5 has been added is excited by monochromatic light at 625 nm with a bandwidth of 10 nm. For such embodiments using CY3 and CY5 dyes, when fluorescing the CY3 dye gives off green light having a peak value at 570 nm, and the CY5 dye gives off red light having a peak value at 670 nm. The excitation of wells with CY3 and CY5 may be performed concurrently. Assay array 102 may be front-side illuminated, or backside illuminated if transparent, for example.

The term monochromatic is a term of art, where of course in theory no excitation source is purely monochromatic. In the examples given, the bandwidth is less than about 1/50 of the center frequency. For some embodiments, the excitation need not be monochromatic in this sense.

Lens system 106 images the light from the array of wells onto sensor array 110. (Lens system 106 may comprise more than one lens element.) Sensor array 110 comprises an array of pixels, but for simplicity of illustration only one pixel, labeled 112, is shown in FIG. 1. Pixel 112 comprises two optical filters, 112a and 112b, where optical filter 112a has a pass band to allow the fluorescence from the DNA sample material to pass through but to substantially reject light outside the frequency range of this fluorescence. Similarly, optical filter 112b has a pass band to allow the fluorescence from the DNA reference material to pass through but to substantially reject light outside the frequency range of this fluorescence.

For example, for embodiments using CY3 and CY5 dyes as discussed above, one of the optical filters, say 112a, is a thin-film micro-optical-filter having a passband centered at about 580 nm with a bandwidth of 40 nm, and the other optical filter, say 112b, is a thin-film micro-optical-filter having a passband centered at about 765 nm with a bandwidth of 40 nm. In this way, a sensor below optical filter 112a is responsive to the DNA material having the CY3 dye, and a sensor below optical filter 112b is responsive to the DNA material having the CY5 dye.

An exploded view of the sensors and circuit for pixel 112 of the embodiment of FIG. 1 is provided as circuit 114, which may be referred to as a differential logarithm circuit. In the embodiment of FIG. 1, photodetector 116a is below optical filter 112a, and photodetector 116b is below optical filter 112b. In the particular embodiment of FIG. 1, photodetector 116a is responsive to the light imaged from the sample DNA material, and photodetector 116b is responsive to the light imaged from the reference DNA material. In the particular embodiment of FIG. 1, photodetectors 116a and 116b are NPN photodetectors, but other embodiments may use other types of photodetectors.

Photodetector 116a is connected in series with two transistors, nMOSFETs (n-Metal-Oxide-Field-Effect-Transistor) 118a and 120a. The drain-source currents for nMOSFETs 118a and 120a are substantially equal to the current sourced by photodetector 116a. The current sourced by photodetector 116a is proportional to the amplitude of the incident light. Transistors 118a and 120a are each diode-connected. When operating in their sub-threshold regions, their gate-to-source voltages are substantially proportional to the logarithm of the current sourced by photodetector 116a, which in turn is proportional to the logarithm of the amplitude of the light incident on photodetector 116a. Similar remarks apply to photodetector 116b, and transistors 118b and 120b, but where photodetector 116b is responsive to incident light from the reference material.

Differential transistor pair 112a and 112b, resistors 124a and 124b, and tail current transistor 126 form a differential amplifier, where the input signals are the gate voltages of transistors 118a and 118b, and the output voltage is taken at the drain of one of the transistors in the differential transistor pair. For the particular embodiment of FIG. 1, the drain on transistor 122b is taken as an output port, labeled as $V_{OUT}$. Denoting the amplitude of the sample incident light by $A_S$ and the amplitude of the reference incident light by the $A_R$, the output voltage may be written as $$V_{OUT} = K \log\left(\frac{A_S}{A_R}\right),$$

where K is some proportionality factor. It should be noted that the above equation for the output voltage is only approximate, and does not serve as an exact expression of the output voltage in terms of $A_S$ and $A_R$.

Other embodiments may employ circuits different from the particular circuit illustrated in FIG. 1. For example, a circuit complementary to circuit 114 may be realized, where pMOSFETs are used instead of nMOSFETs in circuit 114, and PNP photodetectors are used instead of photodetectors 116a and 116b. Furthermore, some embodiments may employ other types of transistors, such as bipolar transistors. As another example, whereas the embodiment for circuit 114 illustrates two diode-connected transistors in series with each photodetector, other embodiments may use a different number of diode-connected transistors. Other embodiments may use other types of differential amplifiers in place of the differential amplifier represented by transistor pair 112a and 112b, resistors 124a and 124b, and tail current transistor 126. For example, some embodiments may employ active devices in place of resistors 124a and 124b, where such active devices have a relatively wide range linear impedance response, or other embodiments may employ a different configuration of transistors to provide the tail current provided by transistor 126.

Figure 5:
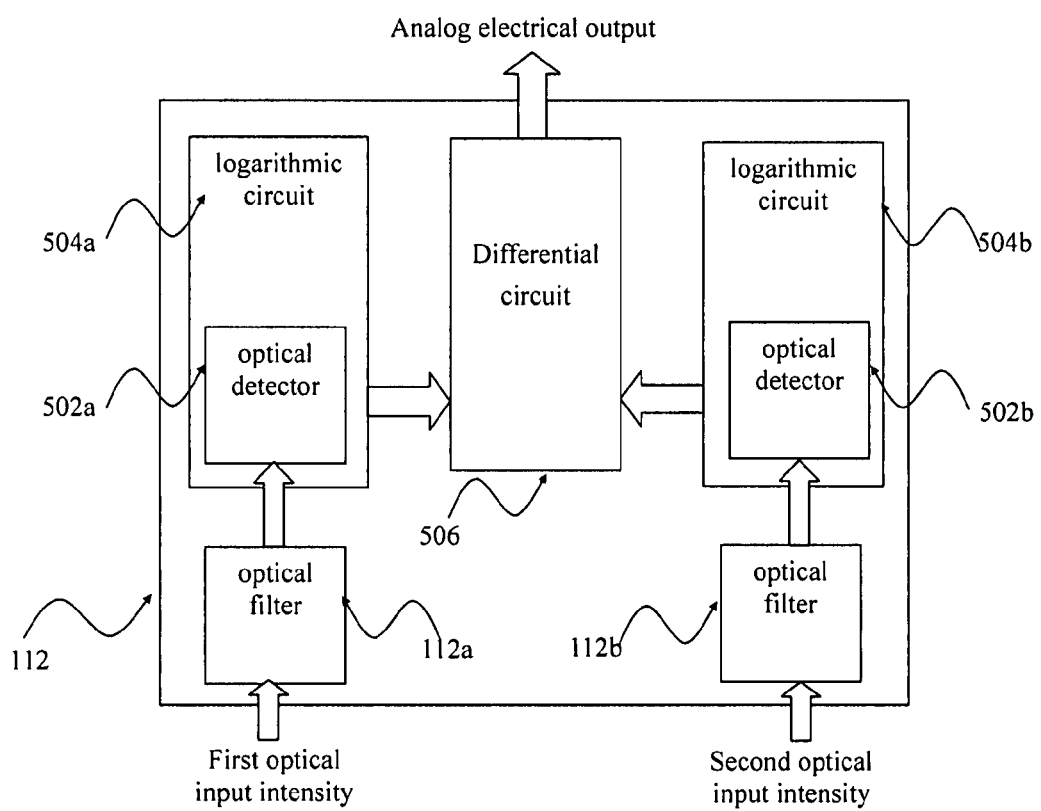
FIG. 5 illustrates a functional block diagram of a pixel according to an embodiment.

Accordingly, pixel 112 may be represented by the functional blocks indicated in FIG. 5. Referring to FIG. 5, optical filter 112a has a first passband to pass to optical detector 502a light that has been filtered by the first passband. The combination of optical detector 502a and logarithmic circuit 504a provides a voltage to differential amplifier indicative of the logarithm of the light intensity provided to optical detector 502a. Similar remarks apply to optical filter 112b, optical detector 502b, and logarithmic circuit 504b, but where optical filter 112b has a second passband different tuned to a different frequency spectrum from that of the first passband. The output of differential amplifier 506 is indicative of the logarithm of the ratio of the light intensities provided to optical detectors 502a and 502b.

Given an array of voltage signals, each voltage signal indicative of the logarithm of the ratio of the sample light amplitude to the reference light amplitude for a particular pair of wells from the assay array, embodiments may use an adaptive neural network to classify the voltage signals. Classification may be viewed as pattern recognition. Some embodiments may employ an adaptive neural network structure such as that illustrated in FIG. 2, where the layer of neurons 202 is a layer of input neurons and the layer of neurons 204 is a layer of output neurons. Input neurons 202 pass on their input to the next layer of neurons, neurons 204, where neurons 204 perform processing on their input.

Figure 2:
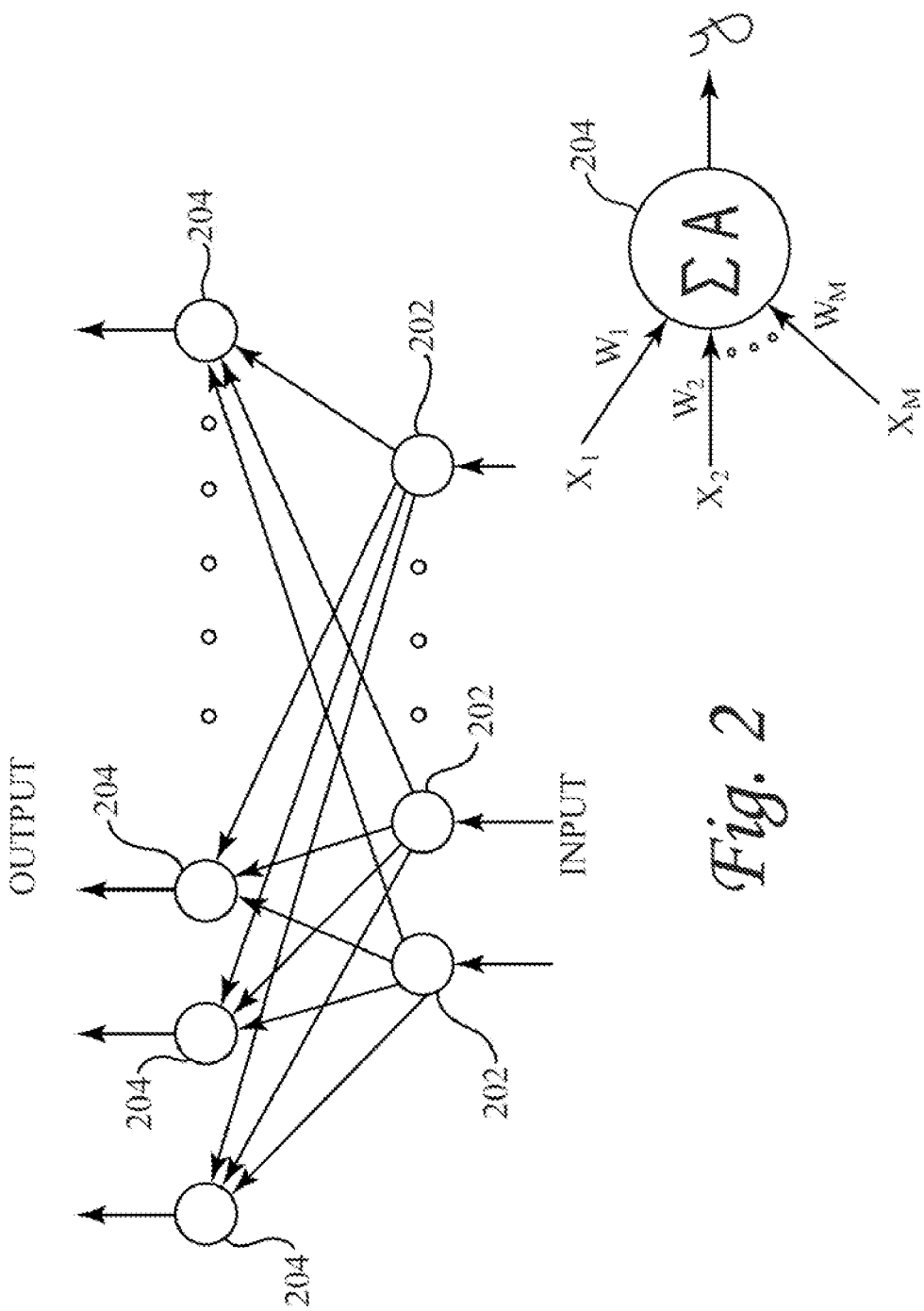
FIGS. 2 and 3 illustrate adaptive neural networks according to an embodiment.

Shown in FIG. 2 is an enlarged view of a neuron 204, indicating a summation function $\Sigma$ using weights $\{w_i, i=1, 2, \ldots, M\}$, and a transfer function A. The integer M denotes the number of inputs to neuron 204, which for the embodiment of FIG. 2 is the number of input neurons 202. Denoting the inputs to neuron 204 as $\{x_i, i=1, 2, \ldots, M\}$, the summation function provides an intermediate term h where $$h = \Sigma_{i=1}^{M} w_i x_i.$$

The weights depend upon the particular output neuron performing the summation, but to avoid multiple subscripts this dependency is not explicitly indicated. For some embodiments, a bias term b may be used, where $$h = \Sigma_{i=1}^{M} w_i x_i - b,$$

where the bias term depends upon the particular output neuron.

The intermediate term h is fed as input to the transfer function A to provide an output y, where in general y=A(h). For some embodiments, A(h) may take the following form:

$$A(h) = \begin{cases} (1+\exp(-h))^{-1} & h < 2 \\ -\alpha\ln(\beta(\delta - h)) & -2 \le h < 0 \\ \alpha\ln(\beta(\delta + h)) & 0 \le h < 2 \\ (1+\exp(-h))^{-1} & 2 \le h \end{cases}$$

where $\alpha$, $\beta$, and $\delta$ are constants. As a particular example for some embodiments, the values $\alpha=0.050095635$, $\beta=1000$, and $\delta=0.01$ have been used in experiments. Sometimes, the transfer function is referred to as an activation function, which is the motivation for using the notation A.

The particular transfer function described above may be termed a sigmoid-logarithmic transfer function, or piecewise sigmoid-logarithmic transfer function. This is to be distinguished from the relatively common sigmoid transfer function where $A(h)=(1+\exp(-h))^{-1}$ for all h.

For some embodiments employing digital processing to perform the adaptive neural network function, the input voltage signals to input neurons 202 are quantized by one or more analog-to-digital converters so that input neurons 202 and output neurons 204 operate in the digital domain. However, other embodiments may be mixed-signal systems, where some processing functions are performed in the analog domain, and some processing functions are performed in the digital domain. Some embodiments may be realized in which almost all functions, or all functions, are performed in the analog domain. For example, the weighted summation performed by a neuron, as well as the transfer function, may be performed in the analog domain using analog multiplier circuits and analog summation circuits.

Figure 3:
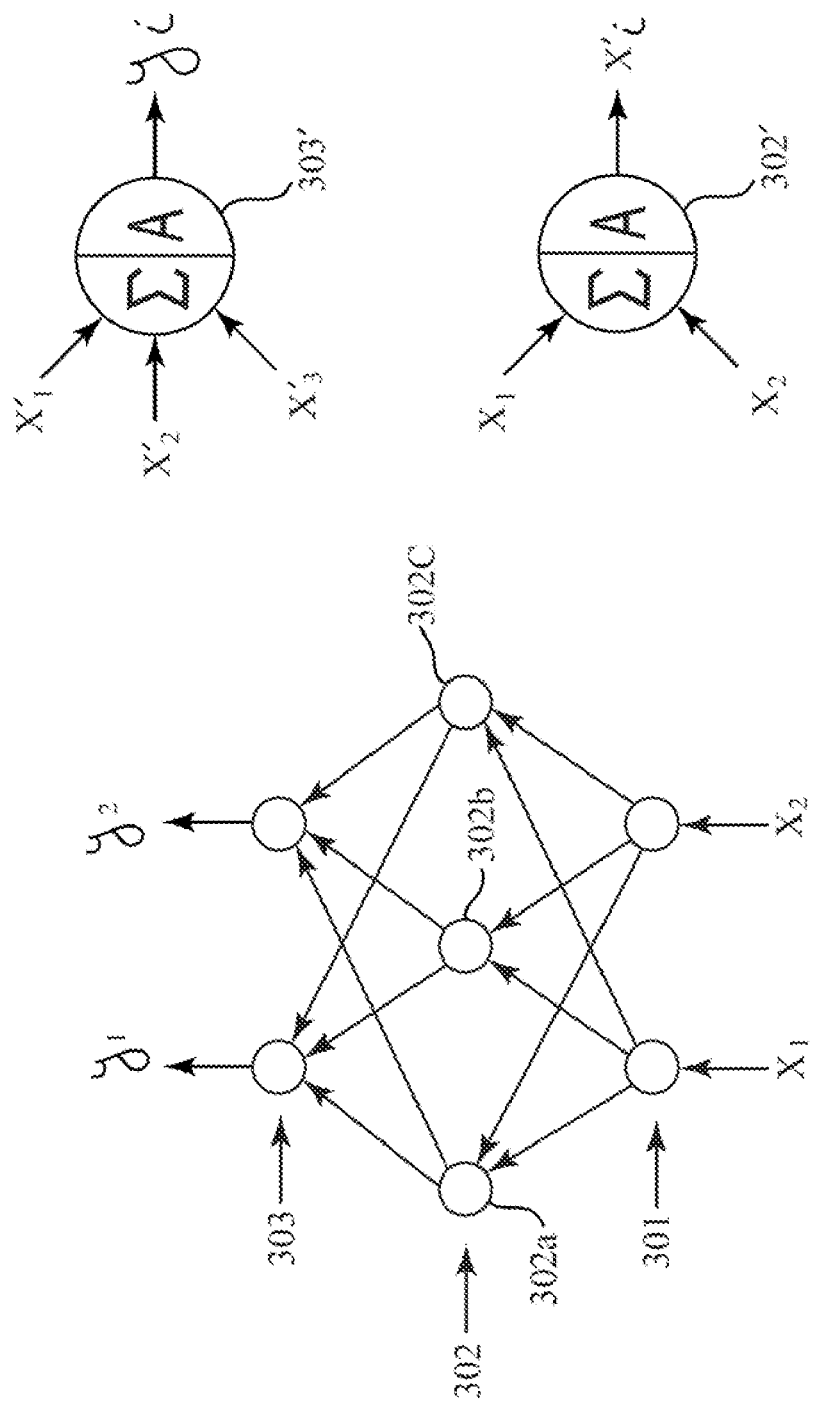

For some embodiments, the adaptive neural network may comprise more than one processing layer, so that there are hidden layers. For example, illustrated in FIG. 3 is an adaptive neural network with two input neurons (layer 301), a hidden layer with three neurons (layer 302), and an output layer with two neurons (layer 303), where neuron 302' is a neuron in hidden layer 302 with transfer function A, and neuron 303' is an output neuron in layer 303 with transfer function A. The adaptive neural network illustrated in FIG. 3 is a feedforward network because there are no feedback paths from a neuron in one layer to another neuron in a preceding layer. Some embodiments, for example, may include feedback paths from layer 303 to layer 302 to implement a recursive adaptive neural network.

In FIG. 3, the inputs are represented by $x_1$ and $x_2$. These are provided as inputs to the hidden layer 302, such as for example neuron 302'. For neuron 302', it is understood that the summation operation operates on two inputs (i.e., the inputs $x_1$ and $x_2$). The output of any one neuron in hidden layer 302 is provided as an input to all neurons in output layer 303. The output of neuron 302' is denoted as $x_i'$, where the index $i=1, 2, 3$ corresponds to neurons 302a, 302b, and 302c, respectively. This output is provided as one of three inputs to each neuron in output layer 303, such as neuron 303'. It is understood that the summation sign in neuron 303' operates on three inputs (i.e., $x_1'$, $x_2'$, and $x_3'$). For some embodiments, the transfer function A may be that as described in the previously displayed expressions for A. The transfer function need not be the same for each layer, but for ease of discussion, the same symbol A is used for neurons in the hidden layer and in the output layer.

During training of an adaptive neural network, a training set of input data is provided, and the weights (and perhaps biases) are updated based upon some desired output and criterion of goodness. For example, suppose for an adaptive neural network there is a set of input variables $\{x_1, x, \ldots, x_N\}$ and a set of output variables $\{y_1, y_2, \ldots, y_N\}$. It is convenient to define an input vector variable $\vec{x}=(x_1, x, \ldots, x_N)$ and an output vector variable $\vec{y}=(y_1, y_2, \ldots, y_N)$. It is also convenient to define particular realizations of these vectors, where we define input vectors $\vec{x}(i)=(x(i)_1, x(i), \ldots, x(i)_N)$ and output vectors $\vec{y}(i)=(y(i)_1, y(i), \ldots, y(i)_N)$, with the index i denoting a particular realization. For example, $\{\vec{x}(i), i=1, 2, \ldots, T\}$ may represent T input training data vectors and $\{\vec{y}(i), i=1, 2, \ldots, T\}$ may represent the resulting T output vectors given by an adaptive neural network for some given set of weights (and also perhaps for some given set of biases). For ease of notation, the dependency of the output vectors on the set of weights (and perhaps biases) is not shown.

During training, for each $\vec{x}(i)$ there is a corresponding desired response vector $\vec{d}(i)$. For example, suppose the pattern recognition function performed by an adaptive neural network is to map the input into one of two classes. That is, there are two patterns to recognize. For a particular example in which there are two output neurons so that the dimension of $\vec{y}$ is N=2, the desired response may be taken as $\vec{d}(i)=(1 0)$ if $\vec{x}(i)$ belongs to one of the two classes, and $\vec{d}(i)=(0\ 1)$ if $\vec{x}(i)$ belongs to the other one of the two classes. A criterion of goodness may be to find the set of weights (and perhaps biases) that minimize the sum of errors e(i) over the training set $\{\vec{x}(i), i=1, 2, \ldots, T\}$, where $e(i)=\|\vec{y}(i)-\vec{d}(i)\|$.

For arbitrarily dimensioned vectors and desired responses, the above-described minimization is a well known mathematical problem, and various mathematical techniques for finding the set of weights (and biases) that satisfy the criterion of goodness are well known. For example, the method of steepest descents may be used, which may be used in conjunction with the error back-propagation neural network learning algorithm, well known in the art of adaptive neural networks.

For an adaptive neural network with a sigmoid-logarithmic transfer function as discussed previously, some embodiments may utilize the back-propagation algorithm for training as follows. First, train the adaptive neural network using a sigmoid transfer function until some criterion of goodness is satisfied. For example, some set of training input vectors $\{\vec{x}(i), i=1, 2, \ldots, T\}$, desired responses $(\vec{d}(i), i=1, 2, \ldots, T)$, and threshold $\Lambda$ is selected, where the initial set of weights are chosen randomly. The back-propagation algorithm is run until $\Sigma_{i=1}^{T} e(i) < \Lambda$ is satisfied. Second, use the resulting weights as an initial set of weights for another training set (which may or may not be different from the first training set), but now where the sigmoid-logarithmic transfer function is used in the back-propagation algorithm.

Once the adaptive neural network has been trained, it may then be operated with static weights (pattern recognition mode) to perform pattern recognition. Post processing may be applied to the output vector from the output neurons. For some embodiments, a winner-take-all module may be applied, whereby the output neuron with the largest output is chosen as the winner. Some embodiments may perform a multiple winner-take-all module, whereby the next "highest" neuron after the winner is selected, and so on for other neurons. The final outcome (result) of the adaptive neural network may be represented by some L bit number, where $L=\lceil \log_2(N) \rceil$, denoting the selected neuron, where the bracket denotes the smallest integer larger than or equal to $\log_2(N)$.

Some embodiments may perform signal processing algorithms other than those described previously. For example, note that the sum $h=\Sigma_{i=1}^{M} w_i x_i$ may be viewed as an inner product of a weight vector $\vec{w}=(w_1, w_2, \ldots, w_M)$ with the input vector $\vec{x}$. The weight vector $\vec{w}$ may also be referred to as a codevector. For some embodiments, a processing neuron finds the square of the Euclidian distance, denoted as d, between an input vector $\vec{x}$ and a codevector $\vec{w}$, that is, $d(\vec{x}, \vec{w})=\|\vec{x}-\vec{w}\|^2$. The function d may be termed a distortion. It is passed on as input to the transfer function. That is, the output of the neuron employing a distortion measure is A(d). For such embodiments in which the distortion is calculated, the winning neuron will have a minimum output. Alternatively, the output may be taken as 1/A(d), so that the winning neuron will have a maximum output.

The weights in the weight vector $\vec{w}=(w_1, w_2, \ldots, w_M)$ are sometimes also referred to as synapse weights. The processing of $\vec{x}\cdot\vec{w}$ or $d(\vec{x},\vec{w})=\|\vec{x}-\vec{w}\|^2$ may be considered as part of a synapse cell, where the neuron cell involves applying the transfer function to the result of the synapse cell. However, there is no conceptual difference whether or not the synapse cell function is considered part of a neuron cell, or is separated out from the neuron cell, although there may be implementation differences in realizing the processing in hardware.

Some embodiments may perform processing other than the inner product $\vec{x}\cdot\vec{w}$ or the distortion $d(\vec{x},\vec{w})=\|\vec{x}-\vec{w}\|^2$, so that more generally, some embodiments may pass on to a neuron some value $f(\vec{x},\vec{w})$ where $f$ is some function mapping two vectors into a number.

Furthermore, some embodiments may employ a learning function other than a conventional back-propagation algorithm commonly used in adaptive neural networks. For example, some embodiments may perform the following processing operations during the learning mode of an adaptive neural network.

Index the weight vectors (codevectors) as $\vec{w}_i$ where the index i refers to the neuron (or synapse cell if that terminology is being used). Furthermore, it is useful to add another index to $\vec{w}_i$ to designate a particular learning iteration, where $\vec{w}_i(t)$ refers to the codevector for neuron i at iteration t.

Associate with each neuron i a winning frequency $f_i$. It is also convenient to index $f_i$ according to the iteration index, so that $f_i(t)$ refers to the winning frequency for neuron i at iteration index t. Following the convention that t=0 for the first iteration, initialize $\vec{w}_i(0)$ by choosing them from a set of random (or pseudorandom) numbers. Set $f_i(0)=1$ for each i.

Compute the distortion $d_i(t)$ (we have also indexed d according to the neuron index and the iteration index) where $d_i(t)=d(\vec{w}_i(t), \vec{x}_i(t))$ for each neuron (note that we have also indexed the input vector $\vec{x}$ to refer to neuron i and the iteration index.) Select the neuron with the smallest distortion and set its output, denoted as $O_i(t)$, as follows (a value of 1 is considered high): $O_i(t)=1$ if $d_i(t)<d_j(t)$, for $1\leq i, j\leq N$, and $O_i(t)=1$ otherwise (there are N neurons). Update the weight vectors (codevectors) with the following frequency-sensitive training rule and associated winning frequency: $\vec{w}_i(t+1)=\vec{w}_i(t)+S(t)O_i(t)[\vec{x}_i(t)-\vec{w}_i(t)]$; where $S(t)=1/f_i(t)$ if $1\leq f_i(t)\leq f_{TH}$, and $S(t)=0$ otherwise; and $f_i(t+1)=f_i(t)+O_i(t)$. S(t) is the frequency-sensitive learning rate, and $f_{TH}$ is the upper-threshold frequency. Notice that only the winning codevector is updated. The training rule moves the winning codevector toward the training vector by a fractional amount which decreases as the winning frequency increases. If $f_i(t)$ is larger than $f_{TH}$, then S(t) is set to zero and no further training will be performed for the corresponding neuron.

The above operations are performed for the set of training vectors. Use of the upper-threshold frequency may avoid codevector under-utilization during the training process for an inadequately chosen initial codebook of codevectors. The selection of the upper-threshold frequency is heuristic and depends on source data statistics and the training sequence. Empirically, an adequate $f_{TH}$ may be chosen to be two to three times larger than the average winning frequency. The initial codebooks may be created from a pseudorandom number generation function.

A feedforward adaptive neural network is amenable to a parallel processing architecture because all of the neurons in any one layer may process data concurrently. If the functionality of providing the inner product, distortion function, or other types of functions involving the weight vector and input vector to a neuron is to be separated out from the neuron and realized by separate circuits, e.g., the synapses as discussed previously, then the previous sentence should be modified to indicate that the synapses for a layer also may process data concurrently. Furthermore, for multiple layers in a feedforward adaptive neural network, there may be further concurrency in the sense that one or more layers (of neurons and synapses) may be processing in a pipelined fashion. As a result, an adaptive neural network is suitable for a VLSI (Very Large Scale Integration) circuit that takes advantage of concurrent (parallel) processing.

Figure 4:
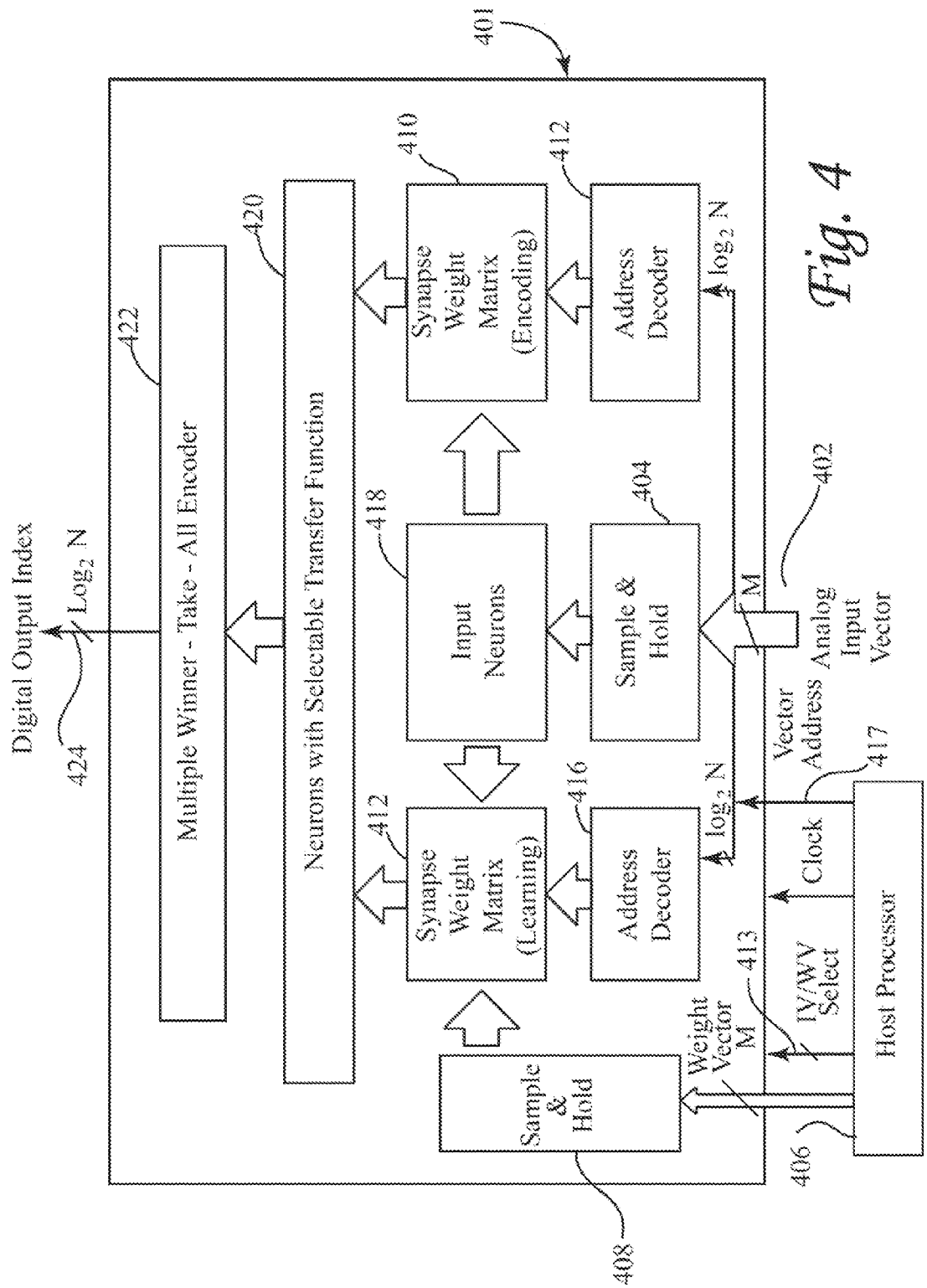
FIG. 4 illustrates functional blocks of a VLSI implementation according to an embodiment.

The functional blocks of VLSI circuit 401 according to an embodiment are illustrated in FIG. 4. The analog voltage signals from the differential logarithmic amplifiers (e.g., the circuit illustrated in FIG. 1) are provided at input port 402. These analog signals are provided to sample and hold 404. Host Processor 406 provides several functions to VLSI circuit 401. For example, host processor provides weight vectors to sample and hold 408. These weight vectors may be the weight vectors obtained after the adaptive neural network has been trained, in which case they are provided to synapse weight matrix unit 410; or they may be the weight vectors that are used for training during a learning mode, in which case they are provided to synapse weight matrix 412. During learning, a training set is provided to input port 402. The term matrix is used in the description for functional units 410 and 412 because the weight vectors may be considered rows (or columns) of a matrix.

Note that for the embodiment of FIG. 4, VLSI circuit performs much of the learning algorithm, so that the parallel processing available from functional units 410, 412, and 420 may be utilized, in which case host process 406 performs some non-parallel learning functions and data-flow control. For some embodiments, all or some of the functions provided by host processor 406 may be integrated on VLSI circuit 401.

Control lines 413 allow host processor 406 to select the sources of input vectors to VLSI circuit 401, and whether weight matrix 410 (pattern recognition mode) or 412 (adaptive or learning mode) are used to store the weight vectors. For example, for some embodiments, if for control lines 413 "IV" (mnemonic for "input vector") is set to a logic 0 (a LOW digital signal value), then the input vector is from the host processor; whereas if "IV" is set to a logic 1 (a HIGH digital signal value), then the input vector is from sensor array 110, that is, the analog output of the differential logarithmic amplifier in circuit 114. If for control lines 413 "WV" (mnemonic for "weight vector") is set to a logic 1, then weight matrix 410 is selected to store weight vectors loaded from host processor

406. These weight vectors are those that are obtained after the learning algorithm has been performed, so that the adaptive neural network is operating in its pattern recognition mode; or they may be the desired response vectors d(i) used in a supervisory learning algorithm when the neural network is operating in its adaptive or (supervisory) learning mode.

The particular weight vector in functional units 410 and 412 for a neuron is addressed by address decoders 414 and 416, where the particular address is provided by host processor 406 by way of vector address bus (lines) 417. Input neurons 418 provides the analog input vector to either synapse weight matrix 410 or 412, depending upon whether the adaptive neural network is in a learning mode or a pattern recognition mode. The latter may be termed an encoding mode, in the sense that an input vector is encoded into a recognizable class. Functional units 410 or 412 perform the synapse function, where for the previously described embodiments may involve forming the inner product of the weight vectors with input vectors, or calculating the distortions. These results are passed to functional unit 420.

Functional unit 420 performs the neuron functions discussed previously, that is, functional unit 420 applies the transfer function to the synapse result. The particular transfer function is selectable. For example, the transfer function may be a sigmoid function, or a sigmoid-logarithm as discussed previously. The outputs of these neurons are provided to functional unit 422, which performs a winner-take-all function, or perhaps selects one among the top several neurons. This result may be encoded into a binary number, provided at output port 424.

Sensor array 110, circuit 114, and VLSI circuit 401 may be integrated on a single die (system-on-chip) for some embodiments, whereas for other embodiments these components may reside on two or more die, or comprise a multi-chip module, for example.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims. Accordingly, various modifications may be made to the described embodiments without departing from the scope of the invention as claimed below.

It is to be understood in these letters patent that the meaning of "A is connected to B", where A or B may be, for example, a node or device terminal, is that A and B are connected to each other so that the voltage potentials of A and B are substantially equal to each other. For example, A and B may be connected together by an interconnect (transmission line). In integrated circuit technology, the interconnect may be exceedingly short, comparable to the device dimension itself. For example, the gates of two transistors may be connected together by polysilicon, or metal interconnect, where the length of the polysilicon, or metal interconnect, is comparable to the gate lengths. As another example, A and B may be connected to each other by a switch, such as a transmission gate, so that their respective voltage potentials are substantially equal to each other when the switch is ON.

It is also to be understood in these letters patent that the meaning of "A is coupled to B" is that either A and B are connected to each other as described above, or that, although A and B may not be connected to each other as described above, there is nevertheless a device or circuit that is connected to both A and B. This device or circuit may include active or passive circuit elements, where the passive circuit elements may be distributed or lumped-parameter in nature. For example, A may be connected to a circuit element that in turn is connected to B.

It is also to be understood in these letters patent that a "current source" may mean either a current source or a current sink. Similar remarks apply to similar phrases, such as, "to source current".

It is also to be understood in these letters patent that various circuit components and blocks, such as current mirrors, amplifiers, etc., may include switches so as to be switched in or out of a larger circuit, and yet such circuit components and blocks may still be considered connected to the larger circuit.

Throughout the description of the embodiments, various mathematical relationships are used to describe relationships among one or more quantities. For example, a mathematical relationship or mathematical transformation may express a relationship by which a quantity is derived from one or more other quantities by way of various mathematical operations, such as addition, subtraction, multiplication, division, etc. Or, a mathematical relationship may indicate that a quantity is larger, smaller, or equal to another quantity. These relationships and transformations are in practice not satisfied exactly, and should therefore be interpreted as "designed for" relationships and transformations. One of ordinary skill in the art may design various working embodiments to satisfy various mathematical relationships or transformations, but these relationships or transformations can only be met within the tolerances of the technology available to the practitioner.

Accordingly, in the following claims, it is to be understood that claimed mathematical relationships or transformations can in practice only be met within the tolerances or precision of the technology available to the practitioner, and that the scope of the claimed subject matter includes those embodiments that substantially satisfy the mathematical relationships or transformations so claimed.

What is claimed is:

1. A system comprising:
   an array of pixels, each pixel comprising:
   a first photodetector;
   a first optical filter having a first passband to pass to the first photodetector a first filtered light having a first intensity;
   a second photodetector;
   a second optical filter having a second passband different from the first passband, the second optical filter to pass to the second photodetector a second filtered light having a second intensity; and
   a first circuit coupled to the first and second photodetectors to provide a voltage indicative of a logarithm of the ratio of the first intensity to the second intensity, wherein the array of pixels has M pixels, where M is an integer greater than one, and the system further comprises a second circuit comprising:
   a functional unit to store a set of weight vectors $\vec{w}_i$, i=1, 2, ..., N, where N is an integer greater than one, each weight vector $\vec{w}_i$ of dimension M, the functional unit to calculate quantities $h_i$, i=1, 2, ..., N where $h_i = f(\vec{x}, \vec{w}_i)$, where $\vec{x}$ is an M dimensional vector of the voltages provided by the first circuit of each corresponding pixel, and $f$ is a function of two M dimensional vectors; and
   a set of N neuron processors, each neuron processor to provide a quantity $A(h_i)$ where A is a selectable transfer function.

2. The system as set forth in claim 1, wherein the selectable transfer function may be selected as:

$$A(h) = \begin{cases} (1+\exp(-h))^{-1} & h < 2 \\ -\alpha\ln(\beta(\delta - h)) & -2 \le h < 0 \\ \alpha\ln(\beta(\delta + h)) & 0 \le h < 2 \\ (1+\exp(-h))^{-1} & 2 \le h \end{cases}$$

where $\alpha$, $\beta$, and $\delta$ are constants.

3. The system as set forth in claim 1, wherein the function $f$ is an inner product function where $\theta(\vec{x},\vec{w}_i)=\vec{x}\cdot\vec{w}_i$.

4. The system as set forth in claim 1, wherein the function $f$ is a distortion function where $\theta(\vec{x},\vec{w}_i)=\|\vec{x}-\vec{w}_i\|^2$.

5. The system as set forth in claim 1, further comprising a die, wherein the second circuit and the array of pixels are integrated on the die.

6. The system as set forth in claim 1, further comprising: an assay array comprising wells; and a lens system to provide an optical path from the assay array to the array of pixels.

7. A system comprising a set of M pixels pixel(i), i=1, 2, ..., M, where M is an integer greater than one, for each i=1, 2, ..., M, pixel(i) comprising:
   a first photodetector(i);
   a first optical filter(i) having a first passband to pass through imaged light to the first photodetector(i);
   a second photodetector(i);
   a second optical filter(i) having a second passband different from the first passband to pass through imaged light to the second photodetector(i);
   a first transistor(i) having a drain connected to the first photodetector(i) and having a gate connected to the drain of the first transistor(i);
   a second transistor(i) having a drain connected to the second photodetector(i) and having a gate connected to the drain of the second transistor(i);
   a third transistor(i) having a gate connected to the gate of the first transistor(i) and having a source; and
   a fourth transistor(i) having a gate connected to the gate of the second transistor(i), having a source connected to the source of the third transistor(i), and having a drain to provide a voltage $x_i$.

8. The system as set forth in claim 7, further comprising:
   a functional unit to store a set of weight vectors $\vec{w}_i$, i=1, 2, ..., N, where N is an integer greater than one, each weight vector $\vec{w}_i$ of dimension M, the functional unit to calculate quantities $h_i$, i=1, 2, ..., N where $h_i=f(\vec{x},\vec{w}_i)$, where $\vec{x}$ is an M dimensional vector with component i equal to the voltage $x_i$, and $f$ is a function of two M dimensional vectors; and
   a set of N neuron processors, each neuron processor to provide a quantity $A(h_i)$ where A is a selectable transfer function.

9. The system as set forth in claim 7, further comprising a die, wherein the functional unit, the set of N neuron processors, and the set of M pixels are integrated on the die.

10. The system as set forth in claim 7, further comprising:
    an assay array comprising wells; and
    a lens system to provide an optical path from the assay array to the set of M pixels.

11. The system as set forth in claim 7, the third transistor (i) having a drain, the system further comprising for each i=1, 2, ..., M, pixel(i):
    a first impedance device(i) connected to the drain of the third transistor(i); and
    a second impedance device(i) connected to the drain of the fourth transistor(i).

12. The system as set forth in claim 8, wherein the selectable transfer function may be selected as:

$$A(h) = \begin{cases} (1+\exp(-h))^{-1} & h < 2 \\ -\alpha\ln(\beta(\delta - h)) & -2 \le h < 0 \\ \alpha\ln(\beta(\delta + h)) & 0 \le h < 2 \\ (1+\exp(-h))^{-1} & 2 \le h \end{cases}$$

where $\alpha$, $\beta$, and $\delta$ are constants.

13. The system as set forth in claim 8, wherein the function $f$ is an inner product function where $f(\vec{x},\vec{w}_i)=\vec{x}\cdot\vec{w}_i$.

14. The system as set forth in claim 8, wherein the function $f$ is a distortion function where $f(\vec{x},\vec{w}_i)=\|\vec{x}-\vec{w}_i\|^2$.

15. The system as set forth in claim 11, wherein for each i=1, 2, ..., M:
    the first impedance device(i) is a first resistor(i); and
    the second impedance device(i) is a second resistor(i).

16. The system as set forth in claim 11, the system further comprising for each i=1, 2, ..., M, pixel(i):
    a tail transistor(i) connected to the sources of the third transistor(i) and the fourth transistor(i).

17. An adaptive neural network, comprising:
    a functional unit to store a set of weight vectors $\vec{w}_i$, i=1, 2, ..., N, where N is an integer greater than one, each weight vector $\vec{w}_i$ of dimension M, where M is an integer greater than one, the functional unit to calculate quantities $h_i$, i=1, 2, ..., N where $h_i=f(\vec{x},\vec{w}_i)$, where $\vec{x}$ is an M dimensional vector, and $f$ is a function of two M dimensional vectors; and
    a set of N neuron processors, each neuron processor to provide a quantity $A(h_i)$ where A is a selectable transfer function, wherein the selectable transfer function may be selected as:

$$A(h) = \begin{cases} (1+\exp(-h))^{-1} & h < 2 \\ -\alpha\ln(\beta(\delta - h)) & -2 \le h < 0 \\ \alpha\ln(\beta(\delta + h)) & 0 \le h < 2 \\ (1+\exp(-h))^{-1} & 2 \le h \end{cases}$$

where $\alpha$, $\beta$, and $\delta$ are constants.

18. The system as set forth in claim 17, wherein the function $f$ is an inner product function where $f(\vec{x},\vec{w}_i)=\vec{x}\cdot\vec{w}_i$.

19. The system as set forth in claim 17, wherein the function $f$ is a distortion function where $f(\vec{x},\vec{w}_i)=\|\vec{x}-\vec{w}_i\|^2$.

* * * * *